(12) United States Patent
Meisel et al.

(10) Patent No.: US 8,673,934 B2
(45) Date of Patent: Mar. 18, 2014

(54) ANTI-INFECTIVE AGENTS AND/OR IMMUNOMODULATORS USED FOR PREVENTIVE THERAPY FOLLOWING AN ACUTE CEREBROVASCULAR ACCIDENT

(75) Inventors: Andreas Meisel, Berlin (DE);
Konstantin Prass, Zachericker Loose (DE); Christian Meisel, Oxford (DE); Elke Halle, Berlin (DE); Ulrich Dirnagl, Berlin (DE); Hans Dieter Volk, Berlin (DE)

(73) Assignees: Hans-Dieter Volk, Berlin (DE); Christian Meisel, Berlin (DE); Andreas Meisel, Oderaue (DE); Ulrich Dirnagl, Berlin (DE); Konstantin Prass, Kummersdorf (DE)

( * ) Notice: Subject to any disclaimer, the term of this patent is extended or adjusted under 35 U.S.C. 154(b) by 1956 days.

(21) Appl. No.: 10/506,598

(22) PCT Filed: Mar. 5, 2003

(86) PCT No.: PCT/EP03/02246
§ 371 (c)(1),
(2), (4) Date: Jun. 3, 2005

(87) PCT Pub. No.: WO03/074057
PCT Pub. Date: Sep. 12, 2003

(65) Prior Publication Data
US 2005/0234089 A1    Oct. 20, 2005

(30) Foreign Application Priority Data

Mar. 5, 2002   (DE) .................................. 102 10 536
Apr. 24, 2002  (DE) .................................. 102 18 328

(51) Int. Cl.
*A61K 31/4709*   (2006.01)
*A61K 45/06*     (2006.01)

(52) U.S. Cl.
USPC ........... 514/300; 514/152; 514/17.7; 514/2.1; 514/2.4; 514/210.09; 514/28; 514/35; 514/376

(58) Field of Classification Search
USPC ...................... 514/35, 300, 152, 210.09, 17.7
See application file for complete search history.

(56) References Cited

U.S. PATENT DOCUMENTS

2001/0043906 A1*  11/2001  Vlasselaer et al. .............. 424/43

FOREIGN PATENT DOCUMENTS

| WO | WO 9612500 A | 5/1996 |
|----|--------------|--------|
| WO | WO 0110465 A | 2/2001 |

OTHER PUBLICATIONS

Mutschler et al., Drug Actions: Basic Principles and Therapeutic Aspects, Oct. 1995 515-519 and 572-576.*
Langhorne et al., Age and Ageing, "What are the Components of Effective Stroke Unit Care?", Sep. 2002.*
Goldstein, Current Treatment Options in Neurology, "Rehabilitation and Recovery After Stroke", vol. 2, No. 4, Aug. 2000.*
Allewelt M et al., "Diagnosis and Therapy of Abscess Forming Pneumonial" *Therapeutische Umschau. Revue Therapeutique.* (2001), vol. 58, pp. 599-603.
"Application of a new fluoroquinolone, moxifloxacin (Avalox®) for the treatment of chronic bronchitis" *Notfall Medizin* (1999), Germany, vol. 25, p. 478, XP009013170.
Chrysos G E et al., "Hospital infections in diabetic patients with cerebral stroke" *International Journal of Antimicrobial Agents* (2001), vol. 17, p. S72, XP001152998.
Giroir BP et al., "Preliminary evaluation of recombinant amino-terminal fragment of human bactericidal/permeability-increasing protein in children with severe meningococcal sepsis" *The Lancet* (1997), vol. 350, pp. 1439-1443.
Database WPI, Section Ch, Week 199908 Derwent Publications Ltd., London, GB; Class B04, AN 1999-081970 XP002246596 & CN 1194828 A (Wang W).
Davenport R J et al., "Complications after acute stroke" *Stroke Online*, vol. 27, pp. 415-420, XP002246595.
Fong I W, "Antibiotics Effects in a Rabbit Model of *Chlamydia pneumoniae*-Induced Atherosclerosis" *The Journal of Infectious Diseases* (2000), United States, vol. 181, pp. S514-S518, XP009013134.
Martynov Yu S et al., "Early and late post stroke pneumonias" *Zhurnal nevropatologii I Psikhiatrii Imeni S S Korsakova*, vol. 80, pp. 1628-1634, XP009013167.
Panella P et al., "Monitoring of low urinary tract infections in patients hospitalized with neurological diseases" Archivio Italiano di Urologia, Andrologia: Organo Ufficiale 'di! Societa Italiana di Ecografia Urologica E Nefrologica/Associazione Ricerche in Urologia, Italy, Dec. 1994. vol. 66, 259-264, XP009013147.
Yrjanheikki J et al., "A tetracycline derivative, minocycline, reduces inflammation and protects against focal cerebral ischemia with a wide therapeutic window" *Proceedings of the National Academy of Sciences of the United States* (1999), vol. 96, pp. 13496-13500, XP002246594.
Davenport R J et al., "Complications after acute stroke" *Stroke Online*, vol. 27, pp. 415-420, XP002246595, Issue 3, Mar. 1996.
Martynov Yu S et al., "Early and late post stroke pneumonias" *Zhurnal nevropatologii I Psikhiatrii Imeni S S Korsakova*, vol. 80, pp. 1628-1634, XP009013167, 1920.

* cited by examiner

*Primary Examiner* — Lezah Roberts
(74) *Attorney, Agent, or Firm* — Saliwanchik, Lloyd & Eisenschenk

(57) ABSTRACT

The invention refers to agents for the preventive therapy after acute stroke, in particular having the aim to prevent infections after stroke. The agents inventively employed in pharmaceutical preparations are anti-infective agents and/or immunomodulating agents, e.g. cytokines and/or inhibitors of the SNS.

9 Claims, 10 Drawing Sheets

15 Mice per Group

Figure 1:
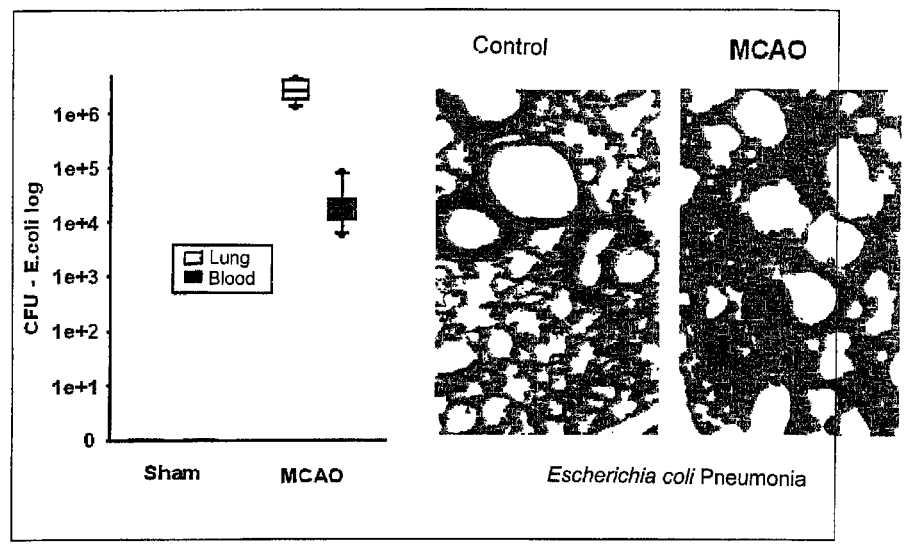

ANTI-INFECTIVE AGENTS AND/OR IMMUNOMODULATORS USED FOR PREVENTIVE THERAPY FOLLOWING AN ACUTE CEREBROVASCULAR ACCIDENT

This application is a National Stage Application of International Application Number PCT/GP03/02246, filed Mar. 5, 2003; which claims priority to German Application No. 102 10 536.7, filed Mar. 5, 2002 and German Application No. 102 10 328.7, filed Apr. 24, 2002.

The invention refers to agents for the preventive anti-infective therapy after acute stroke in order to reduce lethality and morbidity after stroke by preventing infections following an acute stroke event. Infections are severe complications, which commonly occur in the early phase after acute stroke and have a negative prognostic influence. The agents inventively being employed in pharmaceutical preparations are anti-infective agents, in particular antibiotics, which are employed for the prevention and therapy of pneumonias, infections of the urinary tract and sepsis in mammals, in particular in useful animals and domestic animals and also and in particular in the human. The invention moreover refers to agents for the immunomodulating therapy after acute stroke, this approach having the aim to prevent infections after stroke. The agents employed according to the invention in pharmaceutical preparations constitute substances with an immunomodulating potential.

The acute stroke patient, besides the direct consequences of stroke, which may range between transitory or permanent neurological failures and death for reason of encephalothlipsis, in the acute and early remission phase is particularly endangered by infections. Infections, especially pneumonias, constitute the major cause of lethality in stroke (Henon et al. 1995, Katzan et al. 2003, List of References following the examples). Thus, 21-65% of acute stroke patients develop infections and 10-22% develop pneumonias (Davenport et al. 1996, Castillo et al. 1998, Johnston et al. 1998, Grau et al. 1999, Georgilis et al. 1999, Langhorne et al. 2000). The comparison with the incidence of nosocomial infections occurring in an average of 7-10% of all patients (Bucher 2000) and about 3% of postoperative patients (Smyth & Emmerson 2000), particularly underlines the very high frequency of infections in acute stroke patients. In a systematic investigation, it was shown, that the risk of infection is highest at the first and second day after stroke (Grau et al. 1999).

The prevention of stroke-induced infections by means of an immunomodulating and in particular also by means of a preventive anti-infective therapy constitutes a novel approach. In contrast to the instant neuroprotective application of the tetracycline minocycline (Yrjanheikki et al. 1998, 1999), which in particular requires an immediate administration after stroke (up to 4 h after the event), the described application constitutes a retarded treatment scheme (12-72 h), which leads to a reduction of lethality and morbidity via the prevention of severe stroke-induced infections. Tetracyclines moreover are unsuitable for the prevention of the infections typically occurring after severe stroke.

Moxifloxacin belongs to the class of the fluoroquinolones and comprises the active component 1-cyclopropyl-6-fluoro-1,4-dihydro-8-methoxy-7-[(4aS,7aS)-octahydro-6H-pyrrolo[3,4-b]-pyridin-6-yl]-4-oxoquinoline-3-carboxylic acid, which until now was mainly used against infections of the respiratory tract (Zhanel et al. 2002).

Mezlocillin belongs to the class of the acylaminopenicillins and comprises the active component (2S,5R,6R)-3,3-dimethyl-6-((R)-2-[3-(methylsulphonyl)-2-oxo-1-imidazolidin-carboxamido]-2-phenylacetamido)-7-oxo-4-thia-1-azabicyclo[3.2.0]heptan-2-carboxylic acid.

Sulbactam belongs to the class of the β-lactamase inhibitors and comprises the active substance (2S,5R)-3,3-dimethyl-7-oxo-4-thia-1-azabicyclo[3.2.0]heptan-2-carboxylic acid-4,4-dioxide.

Mezlocillin in combination with Sulbactam nowadays is predominantly used for the treatment of systemic or local (multiple) infections and as well for the perioperative short-term prophylaxis (Wright 1999).

The invention has the object, to provide medicinal practice with agents, which are suitable for the preventive therapy after acute stroke. This object in a first aspect is achieved by the purposeful application of anti-infective agents. The invention also has the object, to provide medicinal practice with agents, which are suitable to counteract the immunodepression rapidly setting in after acute stroke and being coincided with a consecutive susceptibility to infection.

This object according to the invention is achieved by the purposeful employment of immunomodulating substances, e.g. of cytokines, inhibitors of the sympathetic nervous system (SNS), inactivated Parapox ovis virus particles or endotoxin binders (rBPI21). According to the invention, medicines for the immunomodulating therapy after acute stroke have been developed, these medicines comprising e.g. cytokines or inhibitors of the SNS, inactivated Parapox ovis virus particles or rBPI21 as active components.

According to the invention, medicines for the preventive therapy after acute stroke have been developed, which—as active components—contain anti-infective substances and/or immunomodulating substances for the prevention and therapy of pneumonias, infections of the urinary tract and sepsis, these active components in particular being selected from the classes of beta-lactam antibiotics, tetracyclines, aminoglycosides, lincosamines, glycopeptides, macrolids, carbapenems, oxazolidinones, streptogramins, from the fluoroquinolones (here in particular from moxifloxacin), from cytokines (interleukins, interferons), inhibitors of the sympathetic nervous system (beta-blockers, alpha-sympathomimetics), endotoxin binders (lipopolysaccharide binding protein=LBP, BPI, rBPI21) and from inactivated Parapox ovis virus particles in pharmaceutical preparations.

It was moreover found, that a cellular-functional immunodepression, which is mainly mediated by the SNS, occurs after stroke, wherein this immunodepression is such severe, that it may lead to the spontaneous development of severe, prognosis-determining infections. The pharmacological suppression of the SNS, the binding of endotoxins, an immunostimulation or the administration of cytokines (within the first 0 to 7 days) can stop this immunodepression and prevent the development of infections. Moreover, an early-stage preventive therapy with anti-infective agents (within the first 0 to 7 days) can lead to a reduction of lethality and morbidity in acute stroke.

According to the invention, a prolonged and severe immunosuppression with early onset (within the first 12 hours) has been recognized in a commonly accepted animal model of stroke (Mouse; occlusion of the *A. cerebri* media (MCAO)—Hata et al. 1998). This immunosuppression becomes obvious on the cellular level on the one hand in the form of a lymphopenia of the T-, B- and NK-cells and on the other hand in functional deficits of monocytes and lymphocytes, among other factors caused by a reduced secretion of the pro-inflammatory cytokine IFN-γ. The immunosuppression is mainly mediated by an overactivation of the SNS.

In the course of 2 to 4 days after stroke, a severe infection spontaneously arises in the animals. This infection is a bacterial sepsis and pneumonia with a lethal outcome in about 60% of the animals. By the inventive early administration of a preventive anti-infective therapy (in case of moxifloxacin within the first 24 h), lethality and the neurological deficit are drastically reduced. In a further aspect of the invention, it is as well possible to prevent the development of infections by a SNS blockade by means of beta-blockers or by the administration of IFN-γ. It was furthermore possible to drastically reduce lethality after acute stroke via an early SNS blockade by means of a beta-blocker.

The preventive therapy with anti-infective agents (e.g. moxifloxacin) within the first 7 days after the onset of disease constitutes a novel therapeutic approach in the treatment of stroke patients, this approach being suitable to reduce the lethality and morbidity of this disease. This in particular provides an effective therapeutic approach for the prevention of the commonly occurring complications of infections.

These complications cause a delayed acute-stationary progress and thus prevent the necessary and effective early-stage rehabilitation. They are to a large extent responsible for the relatively high lethality after acute stroke (Henon et al. 1995, Katzan et al. 2003). These complications lead to fever, another independent risk factor for a negative prognosis after acute stroke (Castillo et al. 1998). The treatment of these complications thus reduces lethality and morbidity after acute stroke.

According to the invention, patients suffering from acute stroke are preventively treated within 72 hours after the onset of symptoms with an antibiotic (moxifloxacin) or several anti-infective agents and are thus prevented from infections (like e.g. pneumonias, infections of the urinary tract and sepsis). This reduces direct and indirect lethality and morbidity. The preventive anti-infective therapy is to be continued for 1-7 days.

The basic idea of the invention is to be found in the use of known means for a novel purpose and in a combination of known elements: the anti-infective agents/antibiotics and a novel effect—their employment for affecting complications of infection by means of an early, preventive anti-infective therapy after acute stroke, this concept in its novel combined effect offering an advantage and the desired result, which are to be found therein, that one can now dispose of means for a preventive therapy leading to a reduction of lethality and morbidity, in particular as well allowing for an improvement of neurological functions after acute stroke.

The invention is moreover directed to the use of anti-infective agents/antibiotics for the preventive anti-infective therapy after acute stroke and for the production of medicines and/or pharmaceutical preparations for the preventive anti-infective therapy after acute stroke.

This comprises their use for the production of medicines for the preventive therapy of pneumonias, infections of the urinary tract and sepsis after acute stroke.

By "early preventive anti-infective therapy after acute stroke" we mean, that the treatment is started within 72 hours after the stroke event.

A further aspect of the invention is given by the immunomodulating therapy with cytokines (e.g. IFN-γ), inactivated parapox viruses (e.g. inactivated Parapox virus ovis), the binding of endotoxin (e.g. by rBPI21) or the blockade of the SNS (e.g. with beta-blockers such as propranolol) or the activation of the parasympathetic nervous system (e.g. CNI-1493) within the first 7 days after the onset of the disease. This aspect constitutes a novel therapeutic approach in the treatment of stroke patients, which is suitable to reduce lethality and morbidity in this disease. In particular, this provides an effective therapeutic approach for the prevention of the frequently occurring complications of infections. These complications lead to a delayed acute-stationary progress, thus preventing the necessary and effective early-stage rehabilitation. These complications are major causes for the relatively high lethality after acute stroke (Henon et al. 1995, Katzan et al. 2003). These complications moreover lead to fever—an independent risk factor for a negative prognosis after acute stroke (Castillo et al. 1998). The prevention of these complications thus reduces lethality and morbidity after acute stroke. In particular, the immunomodulating therapy thereby reduces the neurological deficit.

According to the invention, acute stroke patients are treated within 72 h after the onset of symptoms with a cytokine and/or by a pharmacological blockade of the sympathicus and/or by a pharmacological binding of endotoxin and/or by the activation of the parasympathetic nervous system and/or by immunostimulation, thereby preventing the development of a state of immunodepression and offering protection from infections (like e.g. pneumonias, infections of the urinary tract and sepsis). This allows for a reduction of the direct and indirect lethality and morbidity. This immunomodulating treatment is to be performed from day 0-7 after the acute stroke event, this being dependent on the clinical study performed in the individual case.

The invention's basis idea is given by the use of known means for a novel purpose and by a combination of known elements—the cytokines, immunostimulating agents, anti-sympathicotonic agents and activators of the parasympathetic nervous system—and a novel effect—their application for the prevention of an immunodepression after acute stroke—which in their novel total effect result in a benefit and in the desired success, which is to be found therein, that one can now dispose of means for a preventive therapy leading to a reduction of lethality and morbidity after acute stroke.

The invention is further directed to the use of cytokines and medicines for blocking the SNS, to endotoxin binders and immunostimulating agents for the immunomodulating therapy after acute stroke and as well to the production of medicines and/or pharmaceutical preparations for the immunomodulating therapy of acute stroke.

This comprises their use for the production of medicines for the mitigation or termination of an immunodepression after acute stroke. By "early immunomodulating therapy after acute stroke" we mean, that the therapy is started within 1 week after the stroke event.

DETAILED DESCRIPTION OF THE INVENTION

The invention refers to the use of an anti-infective agent and/or an immunomodulating agent for the production of a medicine and/or a pharmaceutical preparation for the preventive anti-infective therapy after acute stroke. What is developed according to the invention are medicines and pharmaceutical preparations for the preventive therapy after acute stroke, these medicines/preparations containing as active components anti-infective agents for the prevention and therapy of pneumonias, infections of the urinary tract and sepsis, in particular being selected from the classes of the beta-lactam antibiotics, tetracyclines, aminoglycosides, lincosamines, glycopeptides, macrolids, carbapenems, oxazolidinones, streptogramins and fluoroquinolones—here in particular Moxifloxacin—as well as cytokines (interleukins, interferons), inhibitors of the sympathetic nervous system (beta-blockers, alpha-sympathomimetics), activators of the parasympathetic nervous system, endotoxin binders (lipopolysaccharide binding protein=LBP, BPI, rBPI21) and inactive Parapox ovis virus particles in pharmaceutical preparations.

The preventive therapy with anti-invective agents (such as moxifloxacin) within the first 7 days after the onset of disease constitutes a novel therapeutic approach in the treatment of stroke patients, which is suitable to reduce lethality and morbidity of this disease.

The frequently occurring complications of infections cause a delayed acute-stationary progress and thus prevent the necessary and effective early-stage rehabilitation. In addition, they are to a large extent responsible for the relatively high lethality after acute stroke (Henon et al. 1995, Katzan et al. 2003) and moreover give rise to fever, which as an independent risk factor results in a negative prognosis after acute stroke (Castillo et al. 1998). The treatment of these complications thus reduces lethality and morbidity after acute stroke.

According to the invention, patients suffering from acute stroke are treated the earliest possible, at the latest however within 72 hours after the onset of symptoms, with an anti-infective agent, in particular with a broad-spectrum antibiotic, especially with an antibiotic (Moxifloxacin) or a multiplicity of anti-infective agents. This reduces the direct and indirect lethality and morbidity. The preventive anti-invective therapy should be performed for a period of 1-7 days. The preferred dose is adapted to the anti-infective agent's/agents' respective, common daily dose, which is effective for the treatment of the above mentioned infections. The anti-infective agent is preferably administered on the oral or parenteral route. Moxifloxacin is administered in a dose of 400 mg one time per day on the oral or parenteral route.

The anti-infective medicine to be employed may contain one or several antibiotics in a pharmaceutically preparation. In a specific embodiment of the invention, several different anti-infective agents are combined.

Preferred are the antibiotics from the classes of the beta-lactam antibiotics, tetracyclines, aminoglycosides, lincosamines, glycopeptides, macrolids, carbapenems, oxazolidinones, streptogramins and fluoroquinolones. Of these antibiotics, broad-spectrum antibiotics, especially beta-lactam antibiotics, fluoroquinolones and carbapenems are particularly preferred. Most preferred is the application of moxifloxacin (1-cyclopropyl-6-fluoro-1,4-dihydro-8-methoxy-7-[(4aS,7aS)-octahydro-6H-pyrrolo[3,4-b]-pyridin-6-yl]-4-oxoquinoline-3-carboxylic acid), because moxifloxacin is effective in respect to the infective germs emerging in stroke patients and has to be administered just once a day.

The inventive use of an anti-infective agent for the production of medicines and/or pharmaceutical preparations for the preventive anti-infective therapy after acute stroke is useful for mammals, in particular useful animals and domestic animals, but also and in particular for the human. Besides the major use in the field of human medicine, these substances may also be used to produce products and medicines for veterinary medicine.

Preferred is the use of an anti-infective agent in order to provide protection from infections—pneumonias, infections of the urinary tract and/or sepsis—after acute stroke.

According to the present invention, one employs an immunomodulating agent for the production of a pharmaceutical formulation, which immunomodulating agent is characterised in that it may be selected from a group comprising cytokines and/or inhibitors of the SNS and/or activators of the parasympathetic nervous system. These substances have the capacity to prevent or to compensate an immunodepression, in particular the so-called Th1/Th2 shift. The employment of interferons, interleukins and beta-receptor blockers is preferred. The most preferred substances/agents are the β-blocker propranolol, the interferon IFN-γ, the endotoxin binder rBPI-21, the lipopolysaccharide binding protein=LBP and inactivated Parapox ovis virus particles.

According to the invention, the immunomodulating agent (s) are used for the production of a medicine or pharmaceutical formulation, which is useful for the preventive anti-infective therapy after acute stroke in mammals, in particular in useful animals and domestic animals, but also and in particular in the human.

The invention also intends to use one or more anti-infective agents and one or more immunomodulating agents for the production of pharmaceutical preparations for the preventive anti-infective therapy after acute stroke, wherein the anti-infective agent can be selected from the group comprising broad-spectrum antibiotics, and wherein the immunomodulating agent can be selected from the group comprising inhibitors of the SNS, cytokines, endotoxin binders and inactivated Parapox ovis virus particles. In a preferred form, the anti-infective agent is moxifloxacin and the immunomodulating agent is IFN-γ.

The invention may also be realized in the form of a kit, which comprises in a separate or combined form a pharmaceutical composition containing an immunomodulating agent, which can be selected from the group of the cytokines and/or the inhibitors of the SNS and an anti-infective agent, which can be selected from the group of the beta-lactam antibiotics, tetracyclines, aminoglycosides, lincosamines, glycopeptides, macrolids, carbapenems, oxazolidinones, streptogramins and fluoroquinolones.

The invention moreover refers to a method for the treatment of patients after acute stroke, this method having the aim to reduce lethality, thereby also being capable to prevent infections after the stroke. In this treatment method, a patient being in need of such a treatment, i.e. a stroke patient, receives an effective dose of the anti-infective agent and/or the immunomodulating agent. Preferably, the respective dose is administered immediately after the stroke event. It is also possible to administer combinations of one or more anti-infective agents and one or more immunomodulating agents. Preferred are the following combinations of one or more broad-spectrum antibiotics and one or more cytokines and/or endotoxin binders and/or Parapox ovis virus particles. During the following days 1-7, one should use the common daily doses of the above mentioned anti-infective agents (1 mg-100 g) and immunomodulating agents (1 μg-100 g).

The inventive use of the agents can be realized by known formulations, thus by formulations to date being used for the respective active substances. However, the invention also intends to design novel formulations/routes of application being especially suitable for stroke patients, e.g. intrathecal, nasal, intramuscular, intratracheal, intrabronchial, subcutaneous, intravenous, intraarterial, permucosal, enteral and oral forms.

The inventive use of the agents can be realized in known ways by incorporating them into common formulations like tablets, coated tablets, pills, granules, aerosols, emulsions, suspensions and solutions, this being accomplished under the employment of inert, non-toxic, pharmaceutically acceptable carrier substances or solvents. In this context, the agents' therapeutically effective concentration should correspond to concentrations commonly used for these agents so far; or they should be present in concentrations of about 0.1 to 95% by weight, preferably of about 0.5 to 90% by weight of the total composition, i.e. in amounts being sufficient to reach the mentioned dose range. The formulations are e.g. produced by extending the agents with solvents and/or carrier substances, optionally under the employment of emulsifying agents and/or dispersing agents, wherein, e.g. in the case of using water as a diluent, one may optionally use organic solvents as adjuvant substances.

As examples for the adjuvant substances, one may mention e.g. water, non-toxic solvents such as paraffin (e.g. naphtha fractions), plant oils (e.g. peanut/sesame oil), alcohols (e.g. ethanol, glycerol), carrier substances such as natural rock powders (e.g. kaolins, alumina, talcum, chalk), synthetic mineral powders (e.g. highly disperse silica acid, silicates), sugars (e.g. saccharose, lactose and glucose), emulsifying agents (e.g. polyoxyethylene fatty acid esters, polyoxyethylene fatty alcohol ethers), dispersing agents (e.g. lignin, sulphite lyes, methylcellulose, starch and polyvinyl pyrrolidone) and lubricants (e.g. magnesium stearate, talcum, stearic acid and sodium sulphate). The application is usually performed preferably via the oral or parenteral route, in particular perlingually or intravenously. In case of the oral application of the medicines according to the inventions, tablets—besides the mentioned carrier substances—may obviously also contain additives like sodium citrate, calcium carbonate or dicalcium phosphate together with different excipients and filling materials like starch, preferably potato starch, gelatine and the like. Moreover one may also use lubricants like magnesium stearate, sodium lauryl sulphate and talcum for forming the tablets. In case of aqueous suspensions, the active substances—besides the above mentioned adjuvants—may also be mixed with different flavour-improving substances or colorants. In case of the parenteral applications one can employ solutions of the active substances by using suitable liquid carrier materials.

The invention further comprises a kit comprising in a separate form a pharmaceutical composition containing an immunomodulating substance, which may be selected from the above described group of immunomodulating substances and an anti-infective agent, which may be selected from the above described group of the anti-infective agents.

The invention moreover comprises the use of immunomodulating agents and anti-infective agents for the production of a pharmaceutical composition or pharmaceutical medicine containing both substances. Likewise, several substances of both therapeutic groups may be present. Preferred are broad-spectrum antibiotics as well as inhibitors of the SNS and/or activators of the parasympathetic nervous system and/or cytokines and/or endotoxin binders and/or Parapox ovis virus particles.

More preferred combinations are beta-lactam antibiotics, fluoroquinolones and carbapenems and/or cytokines. Most preferred are moxifloxacin and IFN-γ.

The invention will now be further illustrated by means of examples, however without being limited to them.

EXAMPLES ANTI-INFECTIVE AGENT

Example 1A

Mouse Model of Cerebral Ischemia

According to the mouse model of cerebral ischemia, a generally accepted model of ischemic stroke, mice were operated according to the MCAO. In this operation, the *A. cerebri* media is occluded for about 60 minutes, leading to a cerebral infarction typical for this model. As a control, we use the so-called Sham-operation, in which the animals are also MCAO-operated, but in which the *A. cerebri* media is only occluded for about 1 minute. For the rest, the two paradigms are identical. Thus, the perioperative stress can be doubtlessly excluded as a systemic mistake for the following results.

Figure 2:
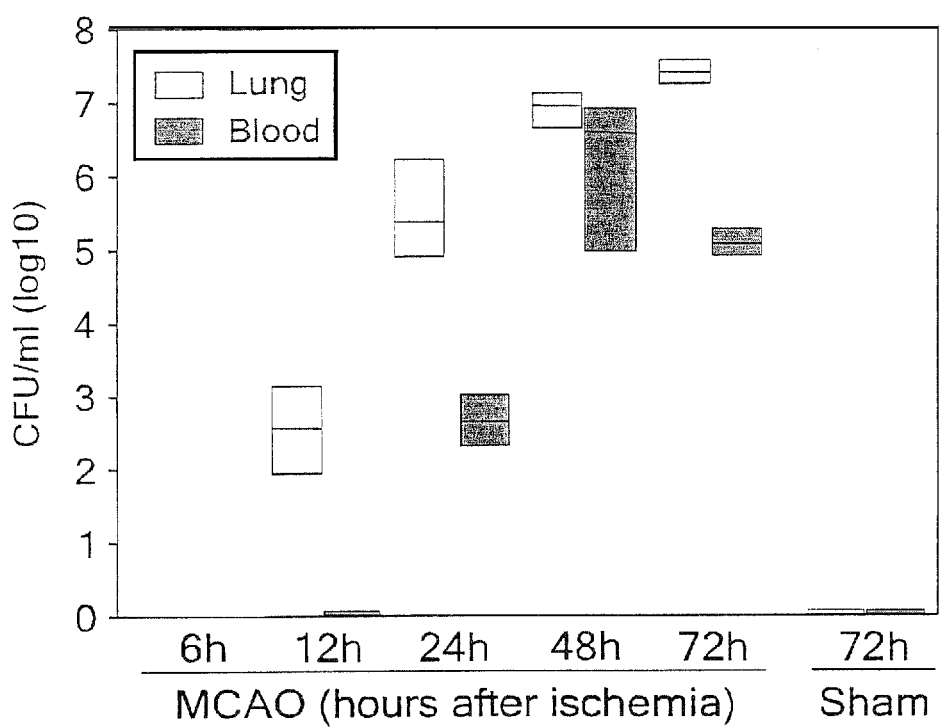

FIG. 1 shows that the mice, 3 days after stroke, suffer from a bacteraemia and a pneumonia with a load of bacterial infection (more than 95% *Escherichia coli*) of $2 \times 10^4$ or, respectively, of $4 \times 10^6$ colony forming units/ml (CFU/ml). In contrast, no infection is found in the control animals (Sham-operated). FIG. 2 shows the typical time course for the stroke-induced spontaneous bacterial infection. A significant load of bacterial infection is observed about 24 hours after stroke.

Figure 3:
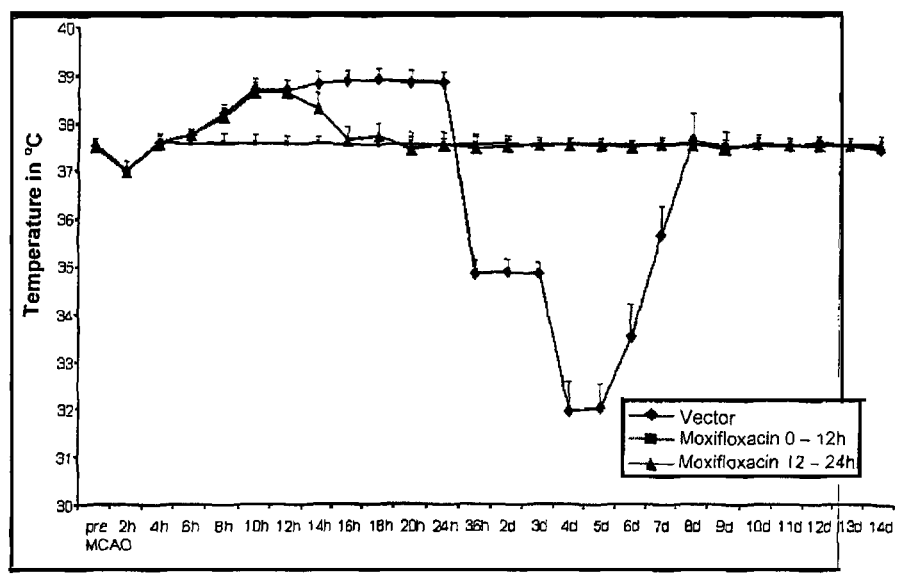
Figure 4:
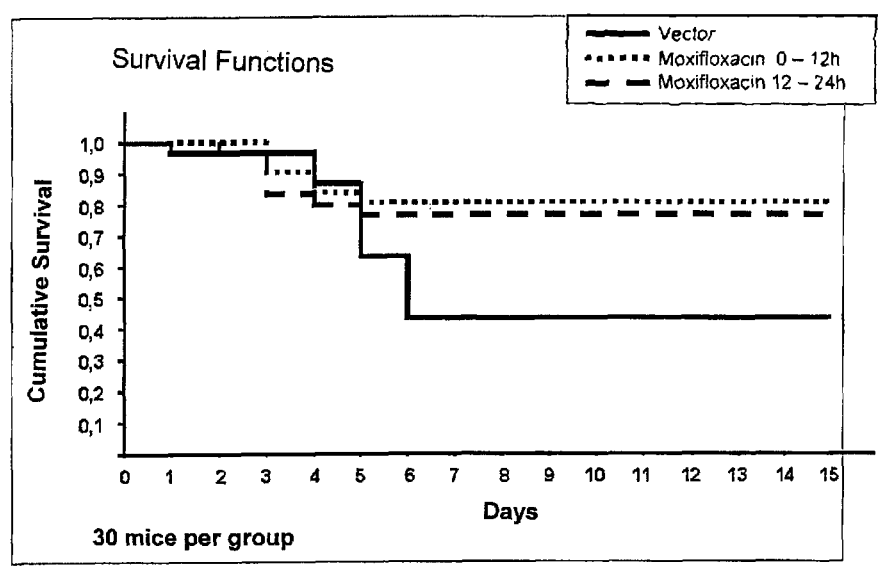

The stroke animals develop fever within the first 12 hours (h) after the stroke event and start to exhibit a hypothermic body temperature after further 12 h (FIG. 3, vector group). In the further process, the bacteraemia/pneumonia proceed to the clinical picture of a sepsis, which leads to death after 4-6 days (FIG. 4, vector group).

Example 2A

Application of an Anti-Infective Agent

By means of a preventive therapy based on the anti-infective agent mezlocillin plus sulbactam, a very early—0 to 12 h after acute stroke—treatment scheme allowed to prevent both the infections (data not shown) and to significantly reduce the fever/hyperthermia and in particular the lethality after stroke.

Example 3A

Application of Mezlocillin plus Sulbactam

By means of a preventive therapy following the principle of example 2, the employment of mezlocillin and sulbactam in a later—12 to 24 h after acute stroke—treatment scheme, both the infections were prevented (data not shown) and the fever/hyperthermia and in particular the lethality after stroke were significantly reduced.

Example 4A

Application of Imipenem Plus Cilastatin

By means of a preventive therapy following the principle of example 2, the employment of imipenem plus cilastatin in a very early—0 to 16 h after acute stroke—treatment scheme, both the infections were prevented (data not shown) and the fever/hyperthermia and in particular the lethality after stroke were significantly reduced.

Example 5A

Application of Moxifloxacin

Figure 5:
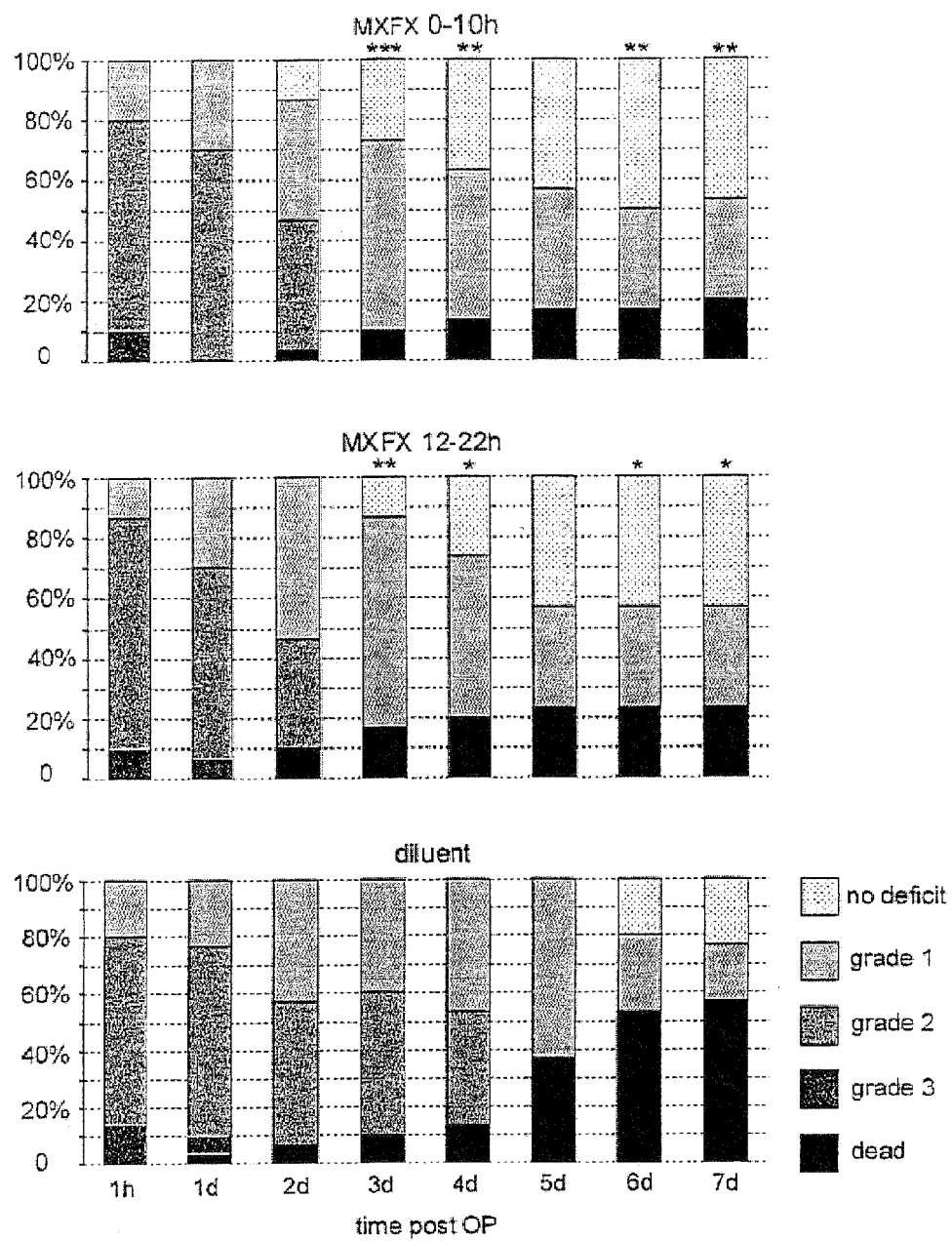

By means of a preventive therapy with moxifloxacin in a very early (0-12 h after acute stroke) and as well in a somewhat later (12-24 h after acute stroke) treatment scheme, both the infections (pneumonia, sepsis) were prevented and the fever/hyperthermia, lethality and in particular also the neurological deficit after stroke were significantly reduced (FIGS. 3 to 5).

EXAMPLES IMMUNOMODULATION

Example 1B

Mouse Model of Cerebral Ischemia

According to the mouse model of cerebral ischemia, mice were operated according to the MCAO. In this operation, the A. cerebri media is occluded for about 60 minutes, leading to a cerebral infarction typical for this model. As a control, we use the so-called Sham-operation, in which the animals are also MCAO-operated, but in which the A. cerebri media is only occluded for about 1 minute. For the rest, the two paradigms are identical. Thus, the perioperative stress can be doubtlessly excluded as a systemic mistake for the following results.

Figure 6:
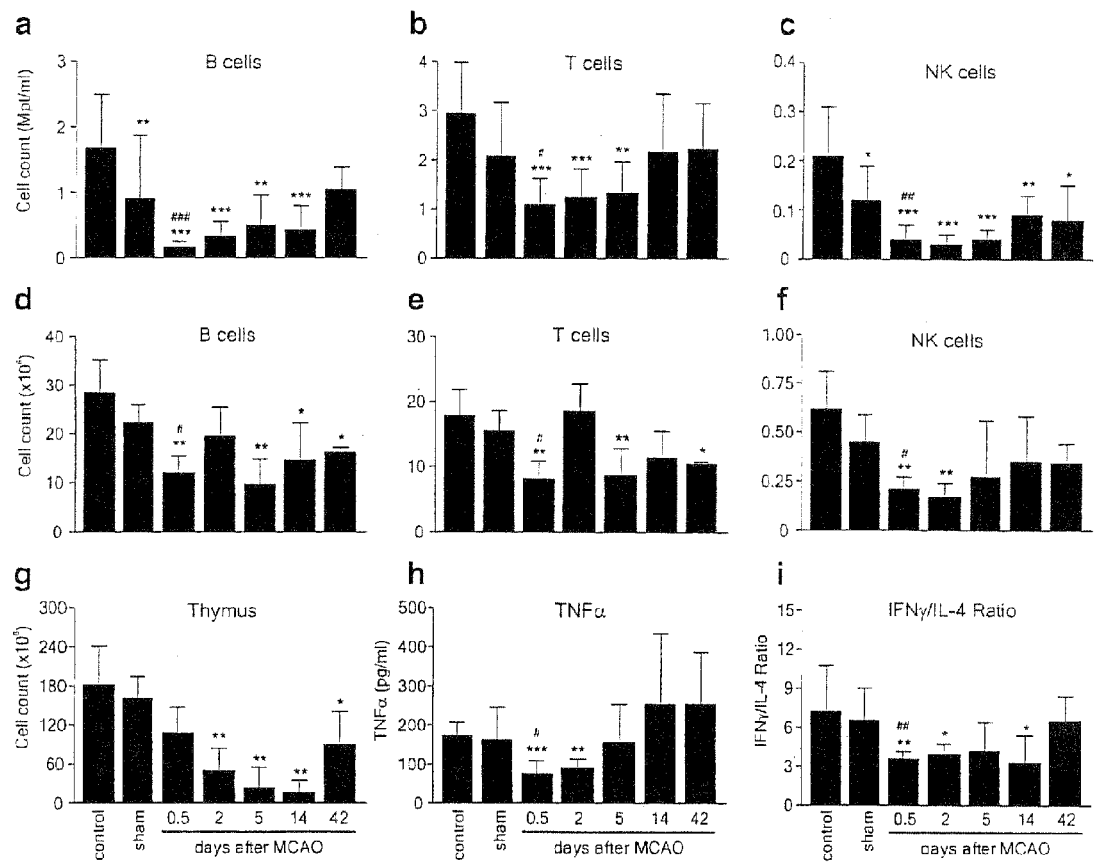

FIG. 6 shows, that the mice within a half day after stroke exhibit a significant reduction in the number of lymphocytes (more detailed: B-cells, T-cells and NK-cells) circulating in the blood (FIG. 6:a-c). This severe lymphopenia persists at least for 14 days and also affects the spleen and the thymus (FIG. 6:d-g), which constitute essential organs of immunological maturation. Besides the mere numeric decrease, there also occurs a functional impairment with a disturbance of the cytokine secretion capacity after stimulation (FIG. 6: h and j). Besides the disturbance of monocyte function, which manifests as a disturbance of TNF-α secretion for 2 days after LPS-stimulation, one can also detect a lymphocyte alteration after ConA-stimulation; this alteration persisting for 14 days after the stroke and mainly causing a Th1- to Th2-shift (alteration of the IFN-γ/IL4 ratio), which means a loss of pro-inflammatory potential. Also the Sham-operated animals exhibit alterations in the above mentioned parameters, but these alterations are smaller. B- and NK-cells only slightly decrease in the blood after the OP-stress. In the spleen and in the thymus, no major stress-induced alterations are detected and the functional parameters of the monocytes and lymphocytes remain at the control level. FIGS. 1 and 2 show that the mice—3 days after the stroke event—exhibit a bacteraemia and a pneumonia with a load of bacterial infection (more than 95% *Escherichia coli*) of $2 \times 10^5$ or, respectively, of $4 \times 10^7$ colony forming units/ml (CFU/ml). In contrast to this, no infection is found in the control animals (Sham-operated).

Example 2B

Figure 7:
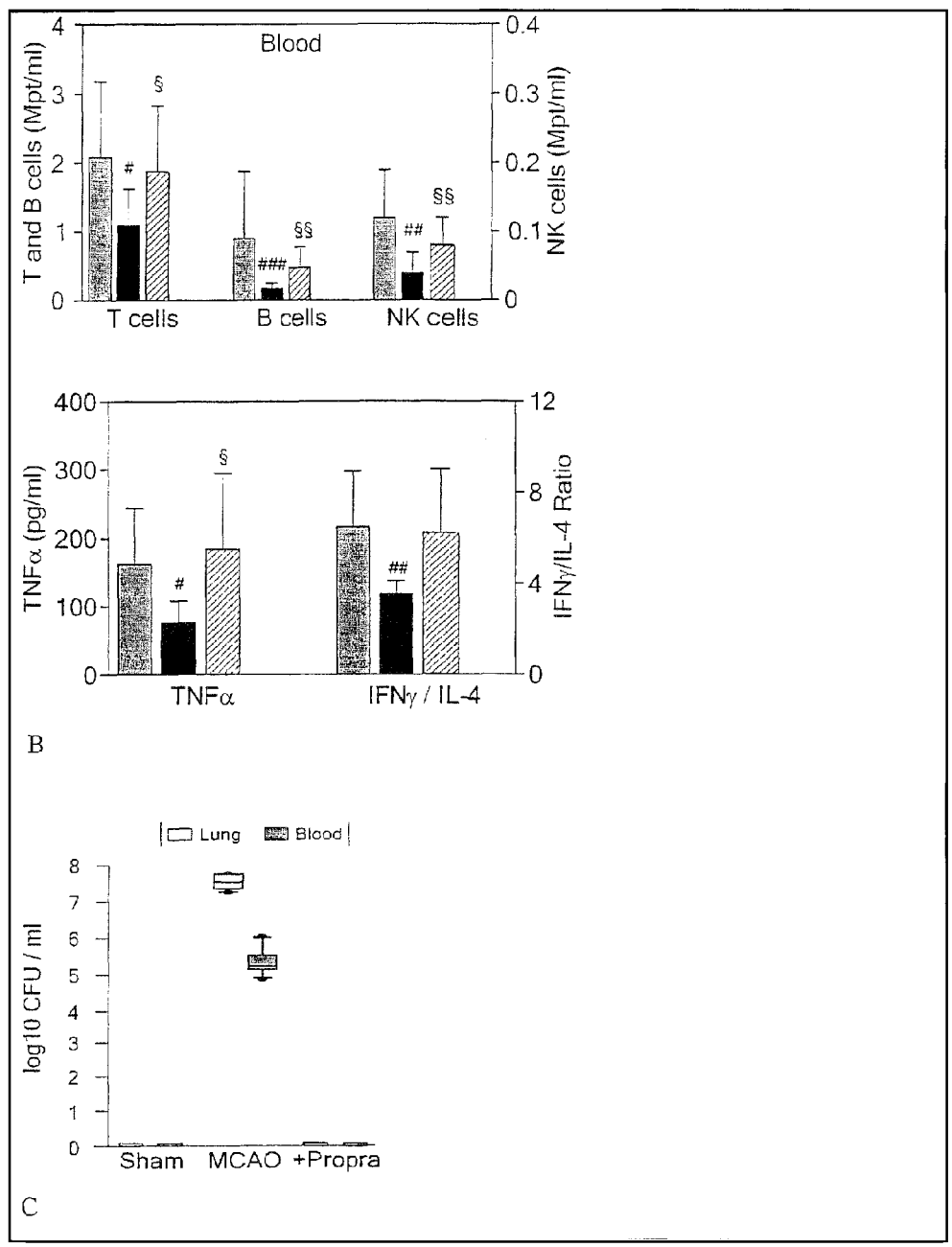
Figure 8:
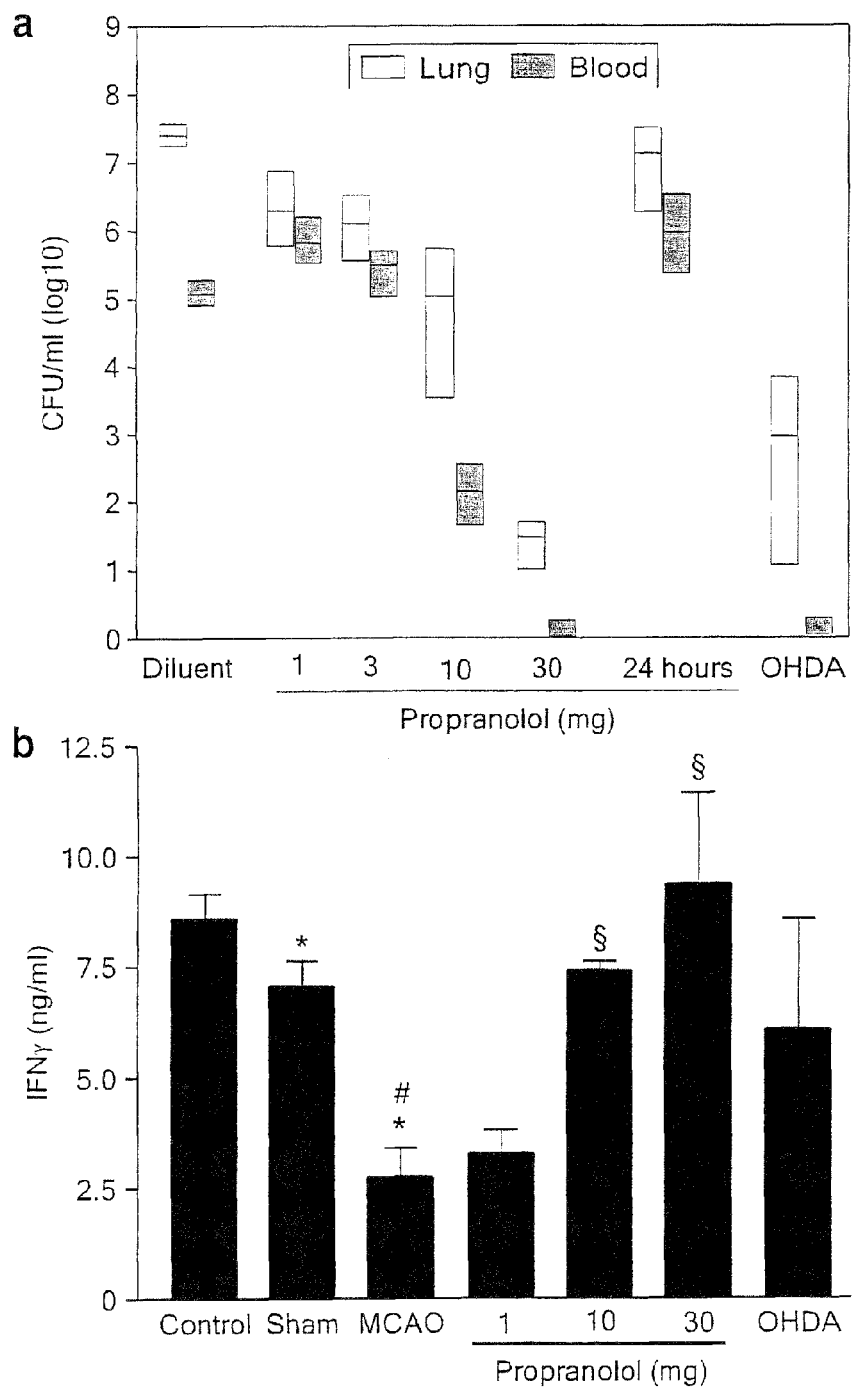

By means of a blockade of the SNS by the administration of propranolol (an unspecific beta-blocker) after experimental stroke in mice, it was possible, to prevent the decrease of T- and NK-cells and to significantly reduce the degree of B-cell lymphopenia (FIG. 7). Furthermore, the blockade of the SNS by propranolol (30 mg/kg body weight) also prevents the disturbance of function of the remaining monocytes (TNF-α secretion) and of the lymphocytes (IFN-γ/IL-4 ratio) (FIG. 7). The SNS blockade can also prevent the development of infections in the lung (pneumonia) and in the blood (sepsis) (FIG. 7). The dose of propranolol (indicated as mg/kg body weight), which is required for the prevention or drastic reduction of the bacterial infections, also prevents the disturbed INF-γ secretion of the lymphocytes (FIG. 8). To this aim, the administration of propranolol has to be accomplished at a very early stage (immediately up to 12 hours) after the stroke. An application 24 hours after the stroke event has no effect (FIG. 8). An early (before the stroke) chemical sympathicolysis by 6-hydroxydopamin (6-OHDA) as well prevents the stroke-induced, disturbed INF-γ function of the lymphocytes and blocks the severe bacterial infections (FIG. 8).

Example 3B

Application of Cytokines

Figure 9:
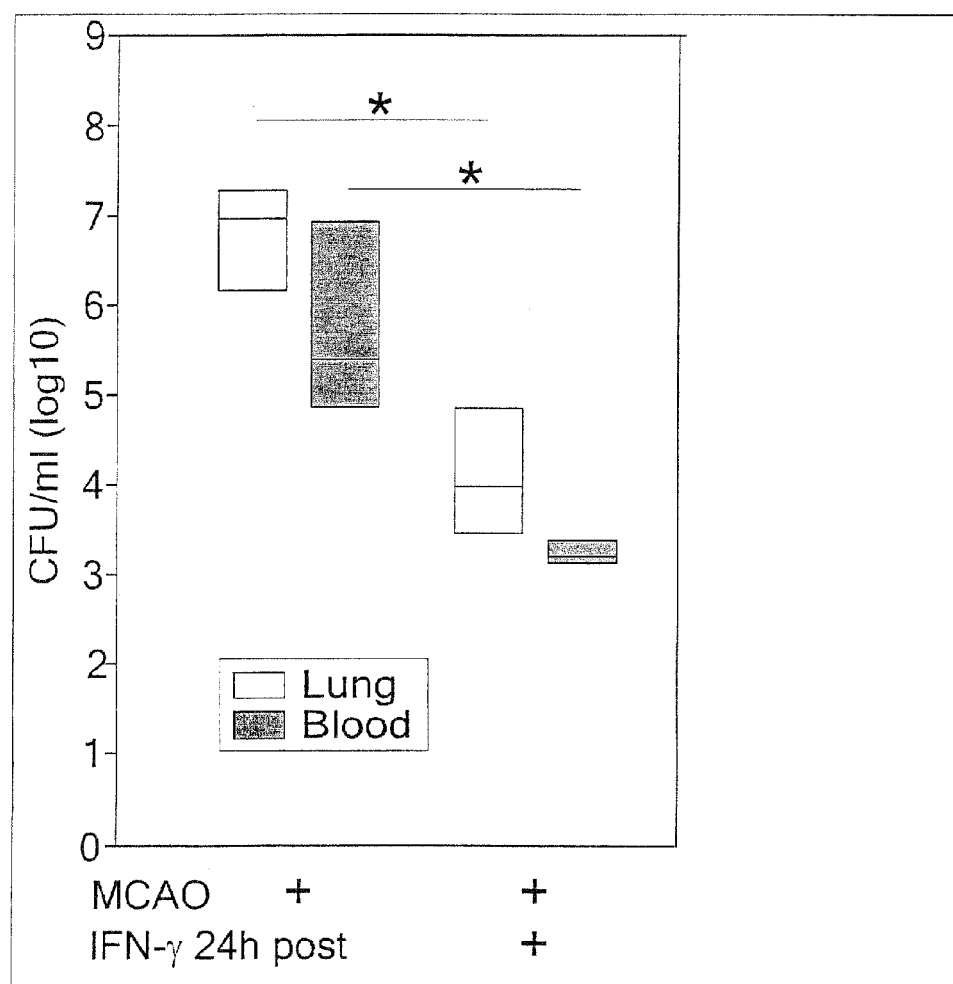

By the application of IFN-γ (2 μg), it was possible to reduce both the germ number in the lung and—even more pronounced—the germ number in the blood (FIG. 9).

Example 4B

Application of a γ-Blocker

Figure 10:
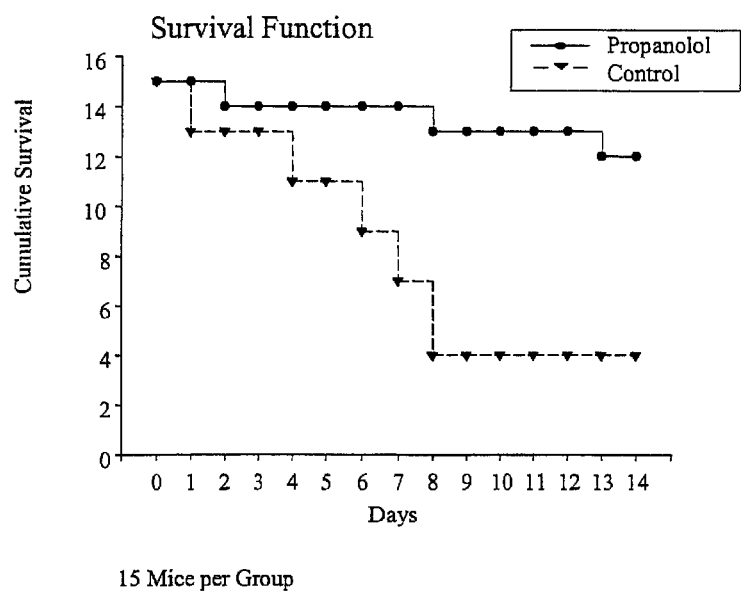

By the application of propranolol (30 mg/kg body weight) it was possible not just to prevent the infections (FIGS. 7 and 8), but also to drastically improve survival after stroke (FIG. 10).

LEGEND TO THE FIGURES

FIG. 1: Bacteraemia and pneumonia 3 days after experimentally induced stroke.

FIG. 2: Early progress of bacteraemia and pneumonia after experimental stroke.

FIG. 1B: Cell separation by FACS-analysis from blood (a-c), spleen (d-f) and thymus (g), and tests of lymphocyte functions for monocytes (h) and T-cells (i).

FIG. 3: Hyper- and hypothermia after experimental stroke and its effective prevention by an early preventive therapy with an anti-infective agent.

FIG. 4: Lethality after experimental stroke and its effective prevention by an early preventive therapy with an anti-infective agent.

FIG. 5: Neurological deficit after experimental stroke and its effective prevention by an early preventive therapy with an anti-infective agent.

FIG. 6: Cell separation by FACS-analysis from blood (a-c), spleen (d-f) and thymus (g), and tests of lymphocyte functions for monocytes (h) and T-cells (i).

FIG. 7: Prevention of the lymphopenia (a), the disturbance of lymphocyte function (b) and the development of severe infections (c) by means of a pharmacological sympathicus blockade.

FIG. 8: Dose- and time-dependent prevention of the development of severe bacterial infections (a) and the disturbance of lymphocyte function (b) by means of a pharmacological sympathicus blockade.

FIG. 9: Attenuation of the severity of infection in the lung and in the blood (number of CFU) by the administration of a cytokine (IFN-γ).

FIG. 10: Lethality after experimental stroke and its effective prevention by an early immunomodulation with a β-blocker.

REFERENCES

Bucher A (2000). Hand hygiene-is hand disinfection the best solution. *Tidsskr Nor Laegeforen* 120:472-5

Castillo J, Dávalos A, Marrugat J, Noya M (1998). Timing for fever-related brain damage in acute ischemic stroke. *Stroke* 29:2455-2460.

Davenport R J, Dennis M S, Wellwood I, Warlow C P (1996). Complications after acute stroke. *Stroke* 27:415-20

Georgilis K, Plomaritoglou A, Dafni U, Bassiakos Y, Vemmos K (1999). Aetiology of fever in patients with acute stroke. *J Intern Med* 246:203-9

Grau A J, Buggle F, Schnitzler P, Spiel M, Lichy C, Hacke W (1999). Fever and infection early after ischemic stroke. *J Neurol Sci* 171:115-20

Hata R, Mies G, Wiessner C, Fritze K, Hesselbarth D, Brinker G, Hossmann K A (1998). A reproducible model of middle cerebral artery occlusion in mice: hemodynamic, biochemical, and magnetic resonance imaging. *J Cereb Blood Flow Metab* 18:367-75

Henon H, Godefroy O, Leys D, Mounier-Vehier F, Lucas C, Rondepierre P, Duhamel A, Pruvo J P (1995). Early predictors of death and disability after acute cerebral ischemic event. *Stroke* 26:392-8

Johnston K C, Li J Y, Lyden P D, Hanson S K, Feasby T E, Adams R J, Faught R E Jr, Haley E C Jr (1998). Medical and neurological complications of ischemic stroke: experience from the RANTTAS trial. RANTTAS Investigators. *Stroke* 29:447-53

Katzan I L, Cebul R D, Husak S H, Dawson N V, Baker D W (2003). The effect of pneumonia on mortality among patients hospitalized for acute stroke. *Neurology* 60:620-5

Langhorne P, Stott D J, Robertson L, MacDonald J, Jones L, McAlpine C, Dick F, Taylor G S, Murray G (2000). Medical complications after stroke: a multicenter study. *Stroke* 31:1223-9

Smyth E T, Emmerson A M (2000). Surgical site infection surveillance. *J Hosp Infect* 45:173-84

Wright A J (1999). The penicillins. *Mayo Clin Proc* 74:290-307

Yrjanheikki J, Keinanen R, Pellikka M, Hokfelt T, Koistinaho J. (1998). Tetracyclines inhibit microglial activation and are neuroprotective in global brain ischemia. *Proc Natl Acad Sci USA* 95:15769-74

Yrjanheikki J, Tikka T, Keinanen R, Goldsteins G, Chan P H, Koistinaho J. (1999). A tetracycline derivative, minocycline, reduces inflammation and protects against focal cerebral ischemia with a wide therapeutic window. *Proc Natl Acad Sci USA* 96:13496-500.

Zhanel G G, Ennis K, Vercaigne L, Walkty A, Gin A S, Embil J, Smith H, Hoban D J (2002). A critical review of the fluoroquinolones: focus on respiratory infections. *Drugs* 62:13-59

The invention claimed is:

1. A method for treating the development of a bacterial infection after acute stroke in order to reduce lethality and morbidity from pneumonia, urinary tract infection, and/or sepsis, wherein said method comprises administering, to a patient who has had a stroke, at least one anti-infective agent comprising at least one antibiotic in a pharmaceutical preparation, wherein said antibiotic is selected from the group consisting of moxifloxacin (1-cyclopropyl-6-fluoro-1,4-dihydro-8-methoxy-7-[(4aS,7aS)-octahydro-6H-pyrrolo[3,4-b]-pyridin-6-yl]-4-oxoquinoline-3-carboxylic acid), mezlocillin, sulbactam and combinations thereof; and optionally at least one immunomodulating agent, and starting the anti-infective therapy within 72 hours following the stroke.

2. The method, according to claim 1, wherein moxifloxacin (1-cyclopropyl-6-fluoro-1,4-dihydro-8-methoxy-7-[(4aS,7aS)-octahydro-6H-pyrrolo[3,4-b]-pyridin-6-yl]-4-oxoquinoline-3-carboxylic acid) is administered to the patient.

3. The method, according to claim 1, wherein said patient is a mammal.

4. The method, according to claim 3, wherein said mammal is a domestic animal or a human.

5. The method, according to claim 1, wherein, at the time of the administration of the anti-infective agent, the patient shows no clinical signs of infection.

6. The method, according to claim 1, wherein the treatment reduces the development of fever in the patient.

7. The method, according to claim 1, wherein the anti-infective agent is administered from 12 hours to 72 hours after the stroke.

8. The method, according to claim 1, wherein the anti-infective agent is administered within 24 hours of the stroke.

9. The method, according to claim 1, wherein the anti-infective agent is administered before any occurrence of bacterial infection.

* * * * *